United States Patent [19]

Heller et al.

[11] 4,344,595

[45] Aug. 17, 1982

[54] AUXILIARY APPARATUS AT A STAND FOR AN OPTICAL OBSERVATION DEVICE

[75] Inventors: Rudolf Heller; Walter Schindler, both of Zürich, Switzerland

[73] Assignee: Contraves AG, Zürich, Switzerland

[21] Appl. No.: 167,540

[22] Filed: Jul. 10, 1980

[30] Foreign Application Priority Data

Jul. 24, 1979 [CH] Switzerland ........................ 6849/79

[51] Int. Cl.³ ............................................ F16M 13/00
[52] U.S. Cl. ................................. 248/542; 248/123.1; 248/280.1; 248/648
[58] Field of Search .................. 248/123.1, 280.1, 325, 248/648, 665, 593, 292.1, 281.1, 542; 350/85

[56] References Cited

U.S. PATENT DOCUMENTS

| | | | |
|---|---|---|---|
| 503,138 | 8/1893 | Hoffstaetter | 188/250 U X |
| 1,020,737 | 3/1912 | Austin | 188/250 R |
| 1,141,322 | 6/1915 | Dodge et al. | 188/250 R |
| 2,967,458 | 1/1961 | Stone | 248/123.1 X |
| 3,217,119 | 11/1965 | Suozzo | 248/542 X |
| 3,311,435 | 3/1967 | Heritage | 248/542 X |
| 3,475,075 | 10/1969 | Stone | 350/84 X |
| 3,722,845 | 3/1973 | Unger | 248/542 |
| 3,809,454 | 5/1974 | Brambring | 350/85 X |
| 3,854,687 | 12/1974 | Sick | 350/85 X |
| 3,891,301 | 6/1975 | Heller | 350/85 |

Primary Examiner—J. Franklin Foss
Attorney, Agent, or Firm—Werner W. Kleeman

[57] ABSTRACT

An auxiliary apparatus at a stand for an optical observation device, such as a surgical microscope is disclosed, which contains a stand at which there is mounted the surgical microscope. The stand comprises a number of rotary and brake bearings, a support arm and a pivotal arm as well as a hinge parallelogram. The surgical microscope or other instrument can be freely adjustable, but fixed in position, throughout a predetermined spatial region as concerns its position and orientation. Arranged at the parallelogram is a web or strap for mounting a support element, at which there is laterally arranged a holder for the attachment of the housing of a brake bearing and a head element. In the head element there is movably mounted by means of a ball hinge element a coupling element structured for receiving and attaching the surgical microscope. In order to level the parallelogram there is arranged a levelling device at the brake bearing and in order to avoid a tilting movement of the parallelogram the suspended microscope is adjustable horizontally and vertically by means of adjustment elements, such as adjustment screws, arranged at the support element.

6 Claims, 2 Drawing Figures

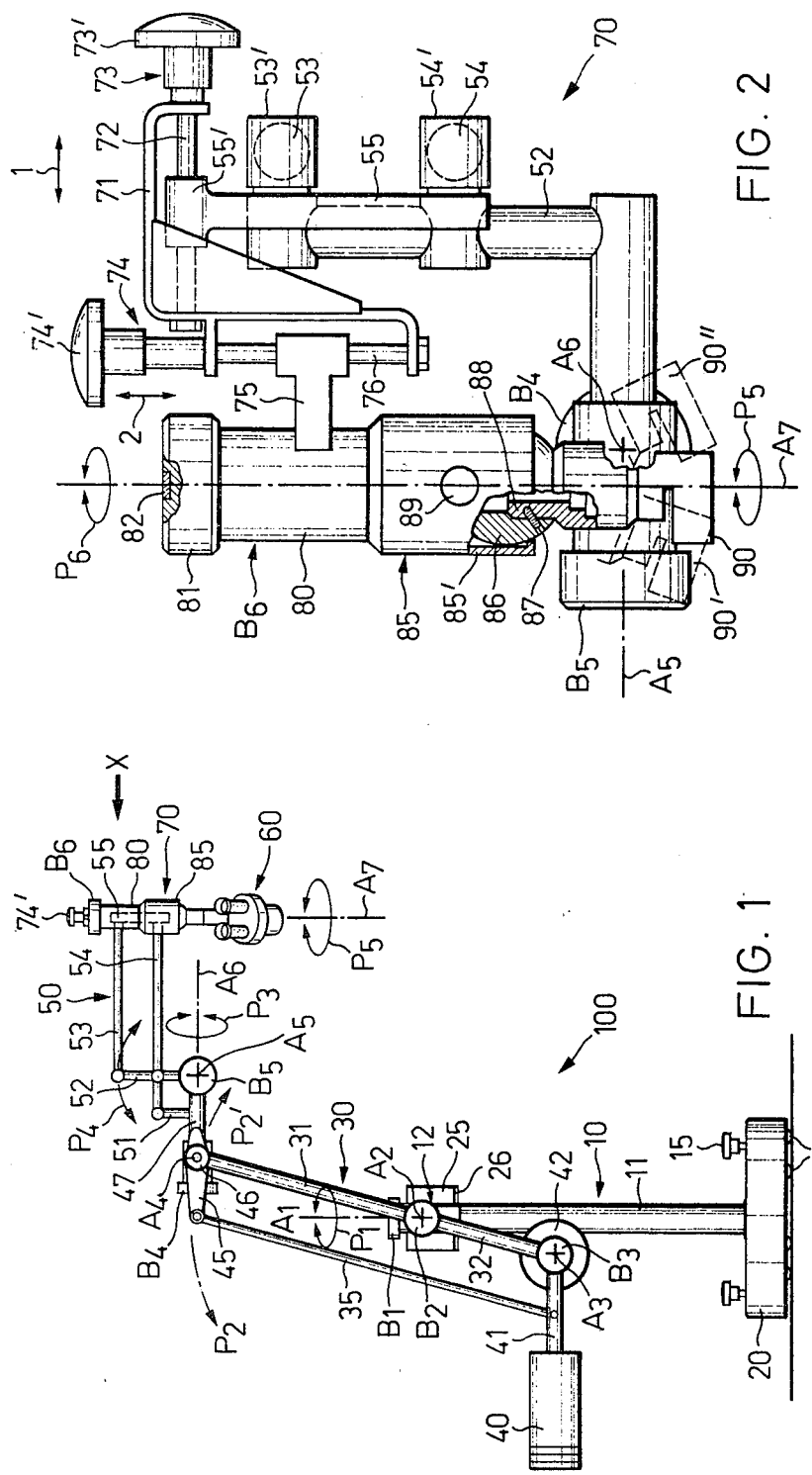

AUXILIARY APPARATUS AT A STAND FOR AN OPTICAL OBSERVATION DEVICE

CROSS-REFERENCE TO RELATED CASE

This application is related to our commonly assigned, copending U.S. application Ser. No. 06/167,538, filed July 10, 1980, entitled "ARRANGEMENT AT A STAND FOR AN OPTICAL OBSERVATION DEVICE".

BACKGROUND OF THE INVENTION

The present invention relates to a new and improved construction of auxiliary apparatus for an optical observation instrument or device, especially for a surgical microscope.

Generally speaking, the auxiliary apparatus is used in conjunction with a stand, at which there is mounted the surgical microscope or other observation instrument. The microscope is arranged at a hinge parallelogram rotatable about a first axis and pivotable about a second axis of a support arm, this second axis being arranged transversely with respect to the first axis. The stand is provided with a number of rotary and brake bearings. The microscope can be freely adjustable, but fixedly positioned, throughout a predetermined spatial region as concerns its position and orientation.

Adjustable supports or stands for optical observation instruments are well known to the art, as evidenced for instance by the commonly assigned U.S. Pat. Nos. 3,762,796, granted Oct. 2, 1973, 3,762,797, granted Oct. 2, 1973, 3,887,267, granted June 3, 1975 and 3,891,301, granted June 24, 1975.

In particular, in Swiss Pat. No. 548,568 and the corresponding U.S. Pat. No. 3,891,301 there is disclosed a support device for a surgical microscope, which is constructed as a stand, wherein for the exchange of different microscopes, or for the mounting of different auxiliary devices at the microscope, for instance for mounting a photographic or television camera, a balancing or compensation weight is displacably arranged upon a support arm of the equipment. This support arm is articulated at the pivotal arm and is oriented essentially horizontally. By means of the balancing or compensation weight it is possible to balance the rotational moment of the suspended microscope. This rotational moment is effective at the relevant rotary and brake bearings and is caused by the weight of the microscope. This measure for compensating the rotational moment by means of the additional compensation weight which, depending upon the size of the microscope and the weight, is cantilevered to a greater extent, is particularly suitable for use with support apparatus of robust or massive construction which are not inhibited by any spatial limitations.

SUMMARY OF THE INVENTION

It is a primary object of the present invention to provide an auxiliary apparatus for a stand for an optical observation device or instrument, which auxiliary apparatus is formed of relatively simple structural means, and with the aid of which auxiliary apparatus it is possible to rapidly and positively adjust the equilibrium state when the load of the observation device is suspended at the hinge parallelogram.

Still a further significant object of the present invention aims at providing a new and improved construction of auxiliary apparatus at a stand for an optical observation device, which is relatively simple in construction and design, economical to manufacture, extremely easy to use, reliable in operation, not readily subject to breakdown or malfunction, and requires a minimum of maintainance and servicing.

Now in order to implement these and still further objects of the invention, which will become more readily apparent as the description proceeds, the auxiliary apparatus of the present development is manifested by the features that at the brake bearing arranged at the front region of the hinge parallelogram there is arranged a levelling element as well as a head element which is rotatable, in relation to the brake bearing, about an axis oriented essentially vertically. At the head element or piece there is movably and fixedly mounted a coupling element structured for receiving and attachment of the observation device. The brake bearing together with the head element and the coupling element are arranged to be adjustable in horizontal direction, in relation to the horizontal first axis of the support arm, and in vertical direction at the hinge parallelogram.

The advantages which can be obtained with the inventive auxiliary apparatus reside in the fact that there can be suspended at the hinge parallelogram of the stand different observation devices with additional photographic or televisions cameras, and without particular expenditure and effort it is possible to manually again re-establish the equilibrium condition of the equipment. Additionally, the auxiliary apparatus, while maintaining an optimum stability, enables realizing a structurally small and light design of the support equipment constructed as a stand.

BRIEF DESCRIPTION OF THE DRAWINGS

The invention will be better understood and objects other than those set forth above, will become apparent when consideration is given to the following detailed description thereof. Such description makes reference to the annexed drawings wherein:

FIG. 1 illustrates in perspective front view a stand containing an auxiliary apparatus and secured at a hinge parallelogram, the auxiliary apparatus serving for receiving an optical observation device; and FIG. 2 illustrates in enlarged view and partially in sectional showing details of the auxiliary apparatus shown in FIG. 1, looking in the direction of the arrow X thereof.

DETAILED DESCRIPTION OF THE PREFERRED EMBODIMENTS

Describing now the drawings, in FIG. 1 reference character 100 designates a mobile floor stand for observation instruments or devices, especially for a surgical microscope, the showing being a front view. The mobile floor stand 100 essentially comprises a stand column 10, a pivotal arm or arm member 30 composed of the partial elements or pieces 31, 32, a support arm 47, and a hinge parallelogram 50 composed of a number of parallelogram elements 51, 52, 53 and 54. The parallelogram or parallelogram means 50 is structured at its front end for receiving and attaching thereat the schematically illustrated surgical microscope 60 or other suitable instrument.

The stand column 10 essentially consists of a stand base or foot portion 20 mounted upon the casters or rollers 21, a preferably tubular-shaped column 11 and a head element or piece 12. The stand column 10 can be levelled and locked in position at the floor or ground by means of fixing bolts or screws 15 or equivalent structure arranged at the base 20. The casters or rollers 21 as well as the fixing bolts or screws 15 are arranged in spaced relationship to one another at a certain geometric distribution within the base or foot portion 20 so as to provide good stability. At the upper region of the column 11 there is arranged the rotatable head piece 12 which can be rotated about a vertical axis $A_1$ in relation to the stationary column 11 in the direction of the double-headed arrow $P_1$. At the head element 12 there is laterally attached a brake bearing $B_2$. Secured to the brake bearing $B_2$ are both of the partial elements 31, 32 of the pivotal arm or arm member 30. This pivotal arm member 30 is pivotable, on the one hand, about the horizontal axis $A_2$ of the brake bearing $B_2$ in the direction of the arrows $P_2$, $P_2'$ and, on the other hand, is rotatable in conjunction with the head element 12 about the vertical axis $A_1$ in the direction of the arrow $P_1$. The pivotal movements $P_2$, $P_2'$ can be manually braked by the brake bearing $B_2$ and the rotational movement $P_1$ by a brake bearing $B_1$.

At the head element or piece 12 there is secured at its outer surface or circumference in offset relationship with respect to the brake bearing $B_2$ an angle member or element 26, serving for receiving an instrument cabinet 25 or the like for the power supply of the optical microscope 60. The cabinet 25 together with the head element 12 and the pivotal arm 30 is rotatable about the vertical axis $A_1$ in the direction of the arrow $P_1$.

At the partial element 32 of the pivotal arm 30 there is arranged at the lower region a brake bearing $B_3$ and a weight or weighting disc 42. Additionally, there is secured at the brake bearing $B_3$ a rod or rod member 41 for receiving a counterweight 40. The partial element 31 of the pivotal arm 30 is provided at its upper region with a bearing 46, at which there is secured a pivotal lever or lever member 45. This pivotal lever 45 as well as the rod or rod member 41 carrying the counterweight 40 are operatively connected by means of a thrust rod 35. This thrust rod 35 extends essentially parallel to the pivotal arm 30 and is hingedly connected at the rod 41 as well as at the pivotal lever 45 in any suitable fashion. The pivotal movements $P_2$, $P_2'$ of the arm or arm member 30 cause a pivotal movement of the lever 45 about the horizontal axis $A_4$ of the bearing 46 as well as the rod 41 together with the counterweight 40 about the horizontal axis $A_3$ of the brake bearing $B_3$, so that the pivotal lever 45 extends parallel to the rod 41 and the thrust rod 35 parallel to the pivotal arm 30 in each position.

Laterally secured to the bearing 46 of the pivotal lever 45 is a brake bearing $B_4$, in which there is rotatably mounted in axial direction the support arm 47 for movement in the direction of the arrow $P_3$. At the end of the support arm 47 there is provided a further brake bearing $B_5$ which is arranged essentially transversely with respect to the brake bearing $B_4$.

The parallelogram 50 composed of the hingedly interconnected parallelogram elements 51, 52, 53 and 54 is hingedly connected by means of the parallelogram element 51 at the support arm 47 and by means of the parallelogram element 52 at the brake bearing $B_5$. Both of the parallelogram elements 53 and 54 of the parallelogram 50 are provided at their respective ends with a respective hinge element 53' and 54', which are interconnected with one another by a strap or web 55, as best seen by referring to FIG. 2. The parallelogram 50 is rotatable in conjunction with the elements 51, 52 which are hinged at the support arm 47 about the axis of rotation $A_6$ of the support 47 in the direction of the double-headed arrow $P_3$ and are pivotable in the direction of the double-headed arrow $P_4$ about the axis $A_5$ oriented transversely with respect to the axis $A_6$ and can be braked by means of the operatively associated brake bearings $B_4$ and $B_5$, respectively.

FIG. 2 shows in front view, looking in the direction of the arrow X of FIG. 1, an auxiliary apparatus 70 arranged at the front region of the parallelogram 50 at the web 55, and which auxiliary apparatus will be described more fully hereinafter.

The web or strap 55 is provided at its upper region with a bearing 55' in which there is mounted a bolt 72 or equivalent structure which carries the auxiliary apparatus 70. This auxiliary apparatus 70 essentially consists of a flexed or bent support element 71, an adjustment screw or bolt 73 or equivalent structure operatively connected with the bolt 72, the adjustment screw having a handgrip 73'. Further, the auxiliary apparatus 70 comprises a bolt 76 arranged and mounted laterally at the support element 71, this bolt 76 or equivalent structure being operatively connected with an adjustment screw 74 provided with a handgrip 74'. At the bolt 76 there is arranged a holder 75 at which there is attached a housing 80 of a further brake bearing $B_6$. Additionally, a head element or piece 85 is rotatably mounted in the housing 80 of the brake bearing $B_6$ and has an axial direction of extent $A_7$. The housing 85' of the head element 85 is structured at the other end, shown partially in sectional view, for the mounting of a ball-and-socket joint element 86. Threadably connected in the ball-and-socket element 86 is a coupling element 90. This coupling element 90 is provided with a threaded portion 88 and serves to receive and attach the microscope 60 and can be fixed by a pin screw 87 or equivalent structure. The coupling element 90 is mounted to be freely movable in the housing 85' of the head element or piece 85. In particular, this coupling element 90 is mounted to be movable by the ball-and-socket joint 86 for the determination of the center of gravity of the suspended microscope 60 throughout a limited, spatial region, as has been schematically illustrated in FIG. 2 by the pivoted partial elements 90', 90'' of the coupling element 90 and can be then fixed in position by a setting or adjustment screw 89 or equivalent structure in the determined center of gravity position. The setting or adjustment screw 89 or the like is arranged at the housing 85'.

The microscope 60, which has not been shown in FIG. 2, and which is suspended at the coupling element 90 and fixed at its center of gravity position, can be rotated, by means of the head piece or element 85 rotatably mounted in the brake bearing $B_6$, about the axis $A_7$ which is essentially vertically oriented, in the direction of the double-headed arrow $P_5$. The braking action of the rotational movement $P_5$ can be adjusted by a conventional brake mechanism provided within the brake bearing $B_6$ and controllable by the rotational movement $P_6$ of the adjustment cap member 81.

As will be further seen from the showing of FIG. 2, mounted at the central region of the adjustment cap member 81, shown partially in sectional view, of the brake bearing $B_6$ is a schematically illustrated levelling element 82, for instance in the form of a bubble level.

In order to compensate the weight of the parallelogram 50 which is articulated at the pivotal arm 47, together with the suspended microscope 60, the brake bearing $B_6$ together with the head element 85 and the coupling element 90 are balanced by means of the levelling element 82—the bubble in the levelling element is positioned so as to be concentrically within the leveling circle—and thereafter the microscope 60 is brought into its center of gravity position and fixed thereat by means of the ball-and-socket joint 86. Then, in order to prevent possibly arising tilting movements of the hinge parallelogram 50 the brake bearing $B_6$ and the elements 89, 90 and 60 are horizontally adjusted in relation to the horizontal axis $A_6$ of the support arm 47 in the direction of the double-headed arrow 1 by means of the adjustment screws 73, 73' and the bolt 72 and in vertical direction, as indicated by the double-headed arrow 2, by means of the adjustment screws 74, 74' and the bolt 76.

At this point it is mentioned that the brake bearings $B_1$, $B_2$, $B_3$, $B_4$, $B_5$ and $B_6$ arranged at the related hinge locations of the stand 100, are structured as conventional rotary and brake bearings and each individual brake bearing can be manually adjusted, so that the brake force which is effective at the rotary and/or pivotal movements of the individual support and pivot arms can be randomly adjusted to the encountered requirements. The brake lining of the conventional and therefore here not particularly illustrated brake mechanisms of the previously mentioned brake bearings preferably has a coefficient of static friction which is as close as possible to the value of the coefficient of sliding friction. It has been found to be particularly advantageous to use as the brake lining one which has been formed of leather.

While there have been shown and described present preferred embodiments of the invention, it is to be distinctly understood that the invention is not limited thereto, but may be otherwise variously embodied and practiced within the scope of the following claims.

Accordingly, what we claim is:

1. An auxiliary apparatus for a stand for an optical observation device, preferably a surgical microscope, comprising:
    said stand containing:
        a support arm;
        a pivotable arm cooperating with said support arm;
        hinge parallelogram means rotatable about a first axis;
        said hinge parallelogram means being pivotable about a second axis of the support arm which is transversely arranged with respect to the first axis;
        a number of rotatary and brake bearings;
        the optical observation device being mounted at the stand and being freely adjustable, but fixedly positionable, in a predetermined spatial region as concerns its position and orientation;
        said hinge parallelogram means having a front region at which there is arranged one of the brake bearings;
        a levelling element provided at said one brake bearing which is arranged at the front region of the hinge parallelogram means;
        a head element mounted to be rotatable in relation to the brake bearing about an essentially vertical axis;
        said head element having a housing;
        a coupling element provided at said head element;
        said coupling element serving for receiving and attaching the observation device;
        said coupling element being mounted to be freely movable in said housing of said head element;
        fixing screw means for fixedly positionally adjusting said coupling element;
        ball-and-socket joint means for mounting said coupling element in said housing of said head element;
        said fixing screw means serving to fixedly positionally adjust said coupling element which is freely movable within the mobility limits of said ball-and-socket joint means; and
        said brake bearing being arranged to be adjustable in horizontal direction, together with the head element and coupling element, in relation to a horizontal axis of the support arm and in vertical direction at the hinge parallelogram means.

2. The auxiliary apparatus as defined in claim 1, wherein:
    said levelling element comprises a bubble level;
    an adjustment cap member provided for said one brake bearing; and
    said bubble level being arranged at a central region of said adjustment cap member.

3. An auxiliary apparatus for a stand for an optical observation device, preferably a surgical microscope, comprising:
    said stand containing:
        a support arm;
        a pivotable arm cooperating with said support arm;
        hinge parallelogram means rotatable about a first axis;
        said hinge parallelogram means being pivotable about a second axis of the support arm which is transversely arranged with respect to the first axis;
        a number of rotary and brake bearings;
        the optical observation device being mounted at the stand and being freely adjustable, but fixedly positionable, in a predetermined spatial region as concerns its position and orientation;
        said hinge parallelogram means having a front region at which there is arranged one of the brake bearings;
        a levelling element provided at said one brake bearing which is arranged at the front region of the hinge parallelogram means;
        a head element mounted to be rotatable in relation to the brake bearing about an essentially vertical axis;
        a coupling element provided at said head element;
        said coupling element serving for receiving and attaching the observation device;
        said brake bearing being arranged to be adjustable in horizontal direction, together with the head element and coupling element, in relation to a horizontal axis of the support arm and in vertical direction at the hinge parallelogram means;
        said hinge parallelogram means has a front region provided with a web;
        a support element mounted at said web; and
        adjustment screw means for adjusting said support element in essentially horizontal direction.

4. The auxiliary apparatus as defined in claim 3, further including:
    holder means arranged laterally of the support element for attaching a housing of said one brake bearing; and adjustment screw means mounted at said support element for vertically adjusting said holder means.

5. The auxiliary apparatus as defined in claim 1, wherein:
each of said rotary and brake bearings contains a brake lining whose coefficient of static friction essentially corresponds to the value of the coefficient of sliding friction.

6. The auxiliary apparatus as defined in claim 5, wherein:
said brake lining of each brake bearing is formed of leather.

* * * * *